United States Patent [19]

Welsh et al.

[11] Patent Number: 4,839,291
[45] Date of Patent: Jun. 13, 1989

[54] DISPOSABLE BIOLOGICAL INDICATOR TEST PACK FOR MONITORING STEAM AND ETHYLENE OXIDE STERILIZATION CYCLES

[75] Inventors: Jon D. Welsh, Fairview; Denis G. Dyke, Edinboro, both of Pa.

[73] Assignee: American Sterilizer Company, Erie, Pa.

[21] Appl. No.: 50,585

[22] Filed: May 15, 1987

[51] Int. Cl.[4] .......................... C12Q 1/22; C12M 1/16
[52] U.S. Cl. ....................................... 435/296; 435/31; 435/299; 435/311; 206/569; 206/305
[58] Field of Search ............... 435/287, 296, 299, 292, 435/293, 294, 295, 296, 311, 31; 206/305, 569

[56] References Cited

U.S. PATENT DOCUMENTS

| | | | |
|---|---|---|---|
| 3,474,003 | 10/1969 | Hirsch | 435/296 |
| 3,661,717 | 5/1972 | Nelson | 435/296 X |
| 3,752,743 | 8/1973 | Hewshilwood | 435/287 |
| 4,291,122 | 9/1981 | Orelski . | |
| 4,304,869 | 12/1981 | Dyke . | |
| 4,579,823 | 4/1986 | Ryder | 435/296 |
| 4,591,566 | 5/1986 | Smith | 435/291 |
| 4,596,696 | 6/1986 | Scoville, Jr. | 435/31 X |
| 4,596,773 | 6/1986 | Wheeler | 435/296 X |
| 4,636,472 | 1/1987 | Bruso | 435/287 |
| 4,717,661 | 1/1988 | McCormick et al. | 435/296 X |

OTHER PUBLICATIONS

Selected pages from "Good Hospital Practice: Steam Sterilization and Sterility Assurance (Proposed Revision)", AAMI Recommended Practice (Nov. 1986 Revision Draft).
"Good Hospital Practice: Performance Evaluation of Ethylene Oxide Sterilizer-Ethylene Oxide Test Packs", Association for the Advancement of Medical Instrumentation (Feb. 11, 1985).
ATI Product Insert for Steam Sterilization Test Pack.
Assert TM Product Inserts for Steam and Ethylene Oxide Sterilization Test Packs.
"Assert TM Single-Use Steam Biological Test Pack Steam Performance Studies", Technical Report 86-4, Surgicot.
Propper Bio Challenge Test-Pak for Steam Sterilization-Advertising Sheet.

*Primary Examiner*—Samuel Scott
*Assistant Examiner*—Carl D. Price
*Attorney, Agent, or Firm*—Kirkpatrick & Lockhart

[57] ABSTRACT

A disposable test pack for monitoring the efficacy of steam or ethylene oxide sterilization cycles includes a fiber board housing for a bioligical indicator. The housing includes an outer tube and a shorter inner tube. The outer tube has upper and lower portions which define a seam or gap at their adjoining open ends. The inner tube extends past the seam and telescopes into the upper and lower portions. The seam and the close tolerance between the inner tube and the upper and lower portions of the outer tube provide a tortuous path for the entry of sterilant into the interior of the housing. The tortuous path has a moisture absorbent surface and is dimensioned to promote intimate contact between the sterilant and the absorbent surface. The exterior of the housing can be lined with foil to prevent sterilant from permeating the housing, thereby preventing entry of the steam by any path other than through the seam. A hole covered by an optionally removable tab is provided at the end of the upper portion of the outer tube for use in monitoring ethylene oxide sterilization cycles.

13 Claims, 4 Drawing Sheets

DISPOSABLE BIOLOGICAL INDICATOR TEST PACK FOR MONITORING STEAM AND ETHYLENE OXIDE STERILIZATION CYCLES

BACKGROUND OF THE INVENTION

1. Field of the Invention

The present invention relates to apparatus for monitoring steam and ethylene oxide sterilization cycles.

2. Description of the Prior Art

A variety of means are available for monitoring the efficacy of sterilization cycles. Standardized spores of a strain sufficiently resistant to the sterilization medium are placed on a substrate and are exposed to the sterilization process. Sterilization of the standardized spore strain provides a high degree of confidence that sterilization of bacterial strains in the chamber load has occurred. Conversely, survival of the standardized spore strain indicates unsatisfactory sterilization of the load. The Association for the Advancement of Medical Instrumentation (AAMI) has published recommendations for evaluating both ethylene oxide and steam sterilizers. Test packs containing biological indicators and other materials are intended to challenge all of the parameters necessary for ethylene oxide or steam sterilization. In actual chamber loads, it may take several minutes into the sterilization cycle before the load is sufficiently exposed to sterilant for sterilization of the load to occur. The test packs should not be sterilized prior to the sterilization of the load. One requirement of a test pack, therefore, is to impede the flow of sterilant to the biological indicator to more closely simulate the rate of sterilization experienced by the load.

Biological indicators are defined by AAMI as a calibration of microorganisms of high resistance to the mode of sterilization being monitored, placed in or on a substrate, packaged to maintain the integrity of the inoculated substrate in a manner convenient to the ultimate user, which serve to demonstrate that sterilization conditions were met. The foregoing definition of biological indicators shall be adopted for purposes of the instant application.

A biological indicator for monitoring the efficacy of ethylene oxide sterilization typically includes Bacillus subtilis spores. A biological indicator for monitoring the efficacy of steam sterilization typically includes Bacillus stearothermophilus spores. However, any microorganism which is highly resistant to the particular sterilization medium will suffice. Vegetative bacteria are known to be easily killed by steam and, thus, are not recommended. Thermotolerant organisms, such as Bacillus spores are known to be extremely resistant. The challenge organism should be more resistant to the sterilant and the population should be greater than the bioburden of the chamber load.

For qualification testing of an ethylene oxide sterilizer, AAMI recommends placing a biological indicator into the barrel of a plastic syringe so that the diaphragm of the plunger does not touch the indicator. The needle end of the syringe must be open. A plastic airway, a length of latex tubing and two such syringes are placed in the center of a stack of folded surgical towels. The stack is then wrapped in a wrapping material. The resulting test pack is designed to challenge the parameters of ethylene oxide sterilization. The towels act as moisture and ethylene oxide absorbents and as a heat sink, the latex and plastic tubes act as ethylene oxide absorbents, and the plastic syringes act as heat sinks, ethylene oxide absorbents and a means for impeding the flow of sterilant to the biological indicators. The biological indicators provide the microbial challenge. The heat sinks are necessary to provide a thermal challenge to the sterilization process. The test pack and, particularly, the environment surrounding the biological indicator should simulate the thermal profile of the normal chamber load. The heat sinks act to slow down the transfer of heat to the spores.

Recommended means for routinely monitoring ethylene oxide sterilization is to wrap the syringe and biological indicator described above in a clean huck towel and seal them in a standard peel pouch. One commercially available monitor includes a plastic syringe which contains a biological indicator and a stack of filter paper discs within the barrel of the syringe. The discs are disposed between the open needle end of the syringe and the biological indicator. The biological indicator includes a plastic ampule with a cap. The cap has a hole in the center to permit the sterilant to enter. A vial of growth media and a spore strip are enclosed in the ampule. Following the sterilization cycle, the ampule is squeezed to break the vial to immerse the spore strip in growth media. The barrel of the syringe is enclosed in a fiber board tube. A chemical process indicator to indicate exposure to ethylene oxide gas is disposed on the fiber board tube. The syringe is placed in a standard peel pouch having a clear plastic sheet heat sealed to a medical grade paper backing which is permeable to the sterilant.

A variety of similar ethylene oxide monitors are commercially available. All are designed to monitor only ethylene oxide sterilization cycles.

A problem sometimes encountered in steam sterilization is air entrapment. Cool air pockets can insulate portions of the load preventing exposure to the sterilant. Very small amounts of air do not impede sterilization as long as the air and steam are thoroughly mixed. When steam contacts cooler objects, the objects absorb the latent heat of the steam, the steam collapses, condensate collects on the objects and any air present remains. Additional steam is drawn to the area and the process is repeated so that air is accumulated and compressed into cool air pockets. Various devices are available to detect critical quantities of air in steam sterilizers. The test packs used to monitor the efficacy of steam sterilization are not designed as air detectors but should be sensitive to air which impedes sterilization. The environment to which the biological indicators are exposed should simulate the sterilizer environment.

The AAMI recommendations for monitoring the efficacy of steam sterilization cycles include using a packaging material which allows adequate air removal to avoid the disproportionate accumulation of air around the biological indicator. The material must also allow steam penetration of the package contents and should provide an adequate barrier to microorganisms. The recommendations for a test pack for use in both gravity-displacement and prevacuum sterilizers include using an appropriate biological indicator in a 14-16 towel test pack. The towels are folded and stacked. The biological indicator should be placed between the 7th and 8th towels in the geometric center of the pack.

A commercially available test pack consists of a small clear plastic tube containing a biological indicator and a chemical process indicator strip. The tube is closed by two plastic caps. A hole at the end of each cap vents the tube and permits the entry of sterilant. Cotton filled gauze covered sponges inside the tube provide means for loosely maintaining the biological and chemical indicators in the midsection of the tube. Loose fitting water-repellent foam discs are disposed at each end of the tube adjacent to the holes in the caps. The dual vent system provided by the opposing holes in the caps is said to mimic the characteristic resistance of the AAMI recommended 14-towel test pack to removal of air by prevacuum or gravity-displacement sterilizer air removal methods. The disposable test pack described is designed for use with steam sterilizers only.

Another type of commercially available steam monitoring test pack, also adapted for use in monitoring only steam sterilization cycles, comprises a stack of filter paper. A cavity is cut out of the center of the stack to house a biological indicator. One manufacturer then wraps the stack of filter paper in a surgical grade paper wrap. Another places the stack in a box. Sterilant entry is from all sides of the stack of filter paper.

A problem with the AAMI recommended procedures is reproducibility from test pack to test pack due to the differences in the quality of towels used and the variance in technique of the persons preparing the test packs. The commercially prepared test packs attempt to standardize the test packs.

An object of the present invention is to provide a single, standardized test pack for use in monitoring the efficacy of both steam and ethylene oxide sterilization cycles. A further object of the present invention is to provide such a test pack which provides a monitor of both steam and ethylene oxide sterilization cycles having the same degree of challenge as the test packs recommenced by AAMI.

SUMMARY OF THE INVENTION

The present invention provides a test pack which represents a sterilant penetration, thermal and microbial challenge to steam and ethylene oxide sterilization processes; monitors the efficacy of both such processes; and provides a reliable, reproducible standard for testing the efficacy of such processes. The test pack of the present invention includes a housing having an interior made of a material having heat sink, insulating and moisture absorbent properties. The housing is preferably made of a cellulosic material, such as fiber board and may be covered on the outside with foil. The housing is configured to define at least one tortuous path for providing entry of sterilant into the housing. This tortuous path has a moisture absorbent surface and is dimensioned to promote intimate contact between the sterilant and the absorbent surface. Means, such as an optionally covered hole in the housing, are provided for optionally providing an alternate path of entry of sterilant into the housing.

The test pack also includes a biological indicator which offers a microbial challenge resistant to sterilization by steam and ethylene oxide sterilants. Means, preferably a carrier, are provided to position the biological indicator within the housing.

The housing is comprised of an inner member and an outer member. The outer member has an upper portion and a lower portion, each of which has one open end in a substantially abutting relationship with the open end of the other portion to define a seam therebetween. The inner member telescopes into the upper and lower portions of the outer member to define at least one tortuous path which progress through the seam, between the outer surface of the inner member and the inner surfaces of at least one of the upper and lower portions and into the housing.

The carrier for positioning the biological indicator has a cutout section for holding the biological indicator and shock absorbing means at its ends.

The seam, and preferably the entire outer member, may be covered with a layer of material, such as medical grade paper, which is permeable to steam and ethylene oxide.

BRIEF DESCRIPTION OF THE DRAWINGS

The present invention will be better understood by reference to the drawings in which.

DETAILED DESCRIPTION OF THE PREFERRED EMBODIMENT

Figure 1:
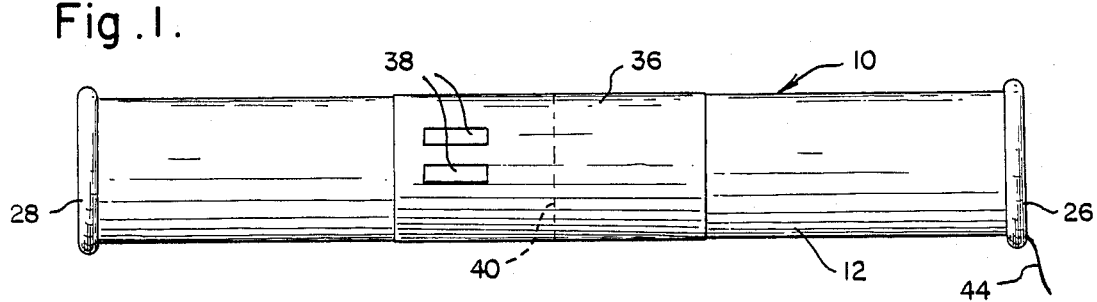
FIG. 1 is a side elevation view of the test pack of the present invention.

The test pack 10 of the present invention provides a single, disposable device for monitoring the efficacy of either a steam or an ethylene oxide sterilization cycle. FIGS. 1 through 12 illustrate the preferred embodiment of test pack 10. As demonstrated by the test data represented hereinbelow and in the graphs of FIGS. 13 through 16, the test pack 10 provides an easy to use sterilization monitor which performs in accordance with the AAMI recommendations for both steam and ethylene oxide sterilization cycles.

Test pack 10 includes generally a housing 12, a biological indicator 60 and means 50 for maintaining the position of biological indicator 60 within housing 12. The housing 12 is constructed of a moisture and ethylene oxide absorbent, insulating cellulosic material, such as fiber board.

Housing 12 includes an outer member, or tube 20 and an inner member, or tube 30. Outer tube 20 has an upper portion 22 open at one end and a lower portion 24, also open at one end.

Housing 12 has at least one tortuous path for entry of sterilant into its interior. In the preferred embodiment, a seam, or gap 40 is defined between the open ends of upper and lower portions 22, 24 of the outer tube 20.

Figure 2:
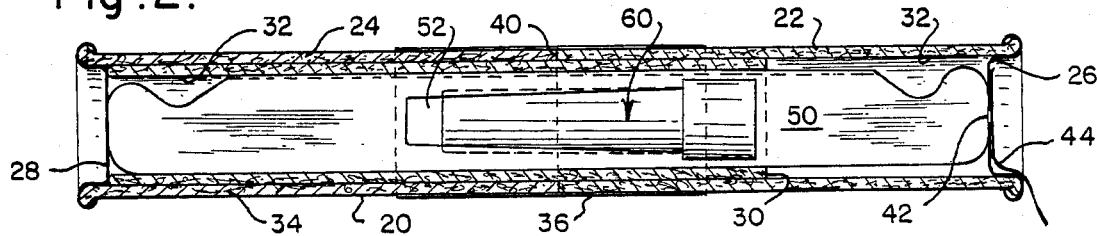
FIG. 2 is a sectional view of the test pack of FIG. 1.
Figure 3:
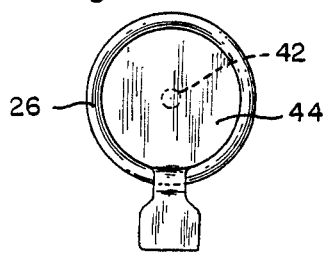
FIG. 3 is an end view of the test pack of FIG. 1.
Figure 4:
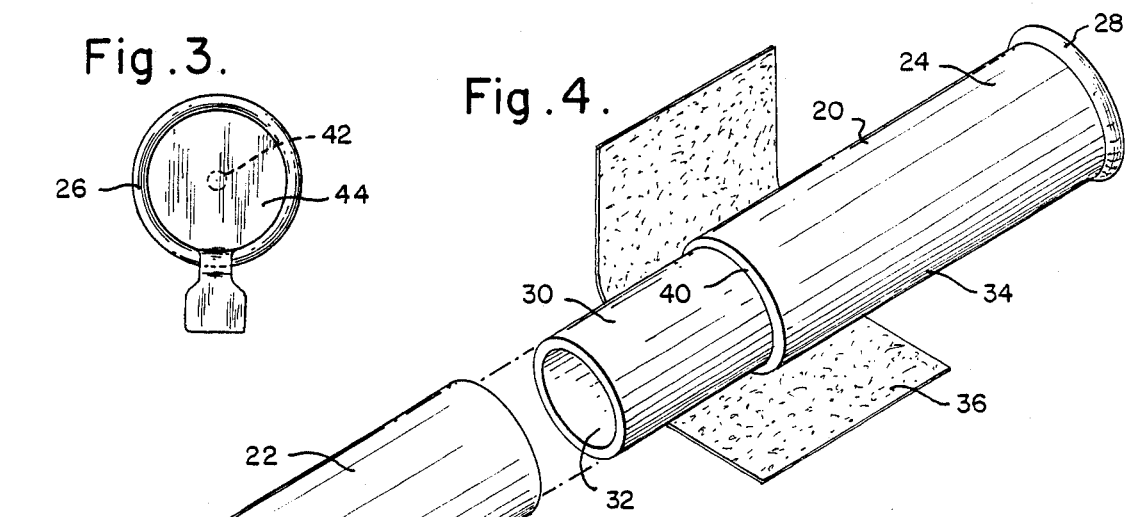
FIG. 4 is an isometric view of an opened test pack.
Figure 5:
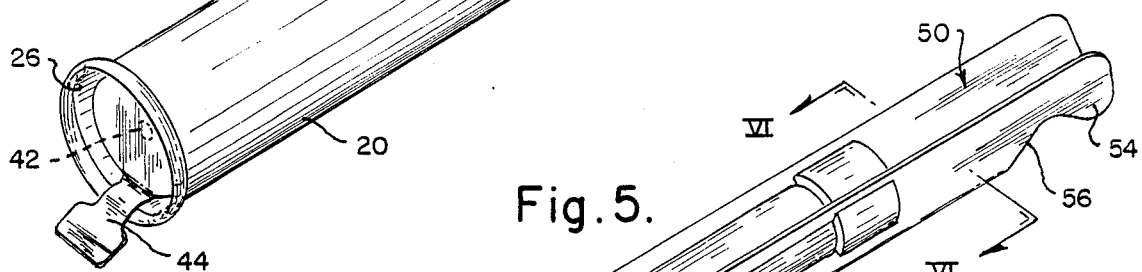
FIG. 5 is an isometric view of the carrier and the biological indicator of the present invention.
Figure 6:
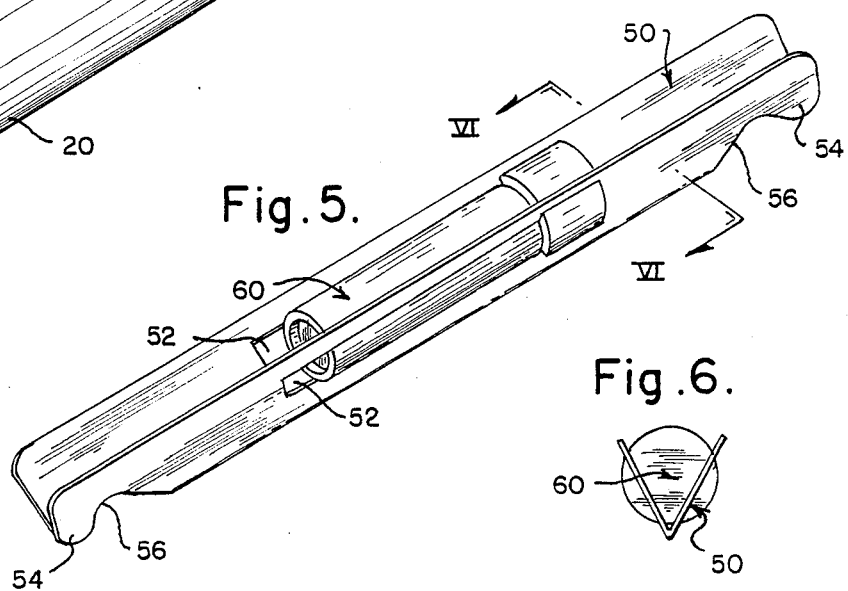
FIG. 6 is a sectional view of the carrier and the biological indicator taken along the line VI—VI in FIG. 5.
Figure 7:
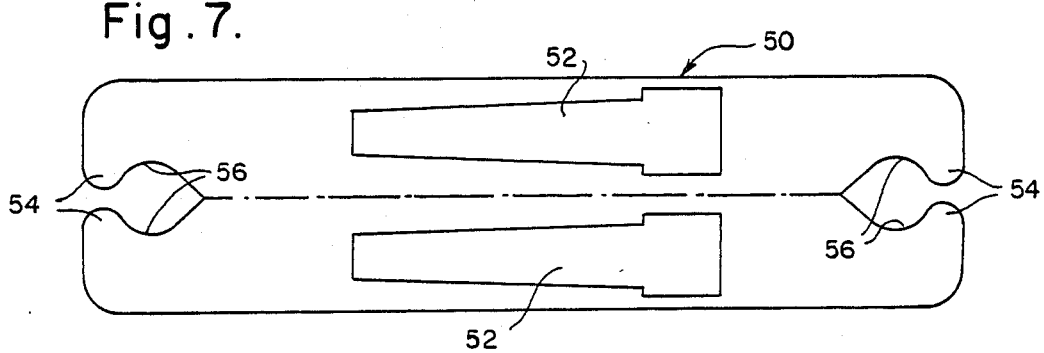
FIG. 7 is a plan view of the carrier of FIG. 5.
Figure 8:
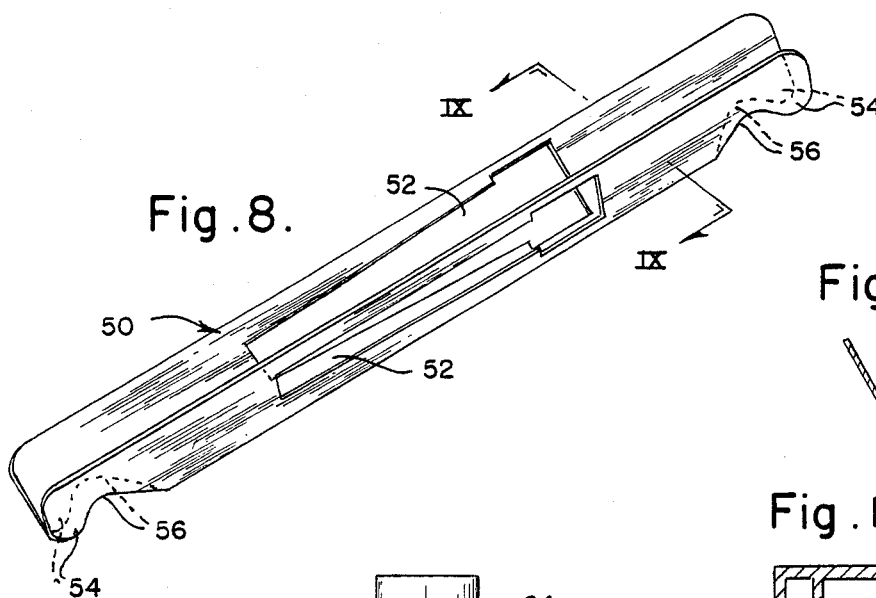
FIG. 8 is an isometric view of the carrier.
Figure 9:
FIG. 9 is a sectional view of the carrier along the line IX—IX of FIG. 8.
Figure 10:
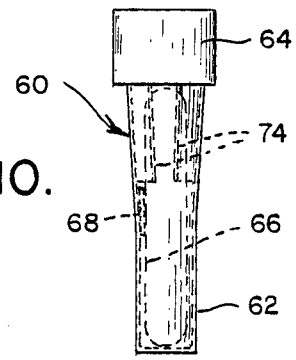
FIG. 10 is a side elevation view of the biological indicator.
Figure 12:
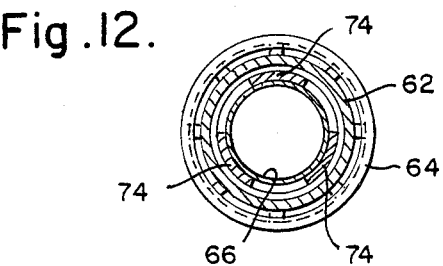
FIG. 12 is a sectional view of the biological indicator along the line XII—XII of FIG. 11.
Figure 11:
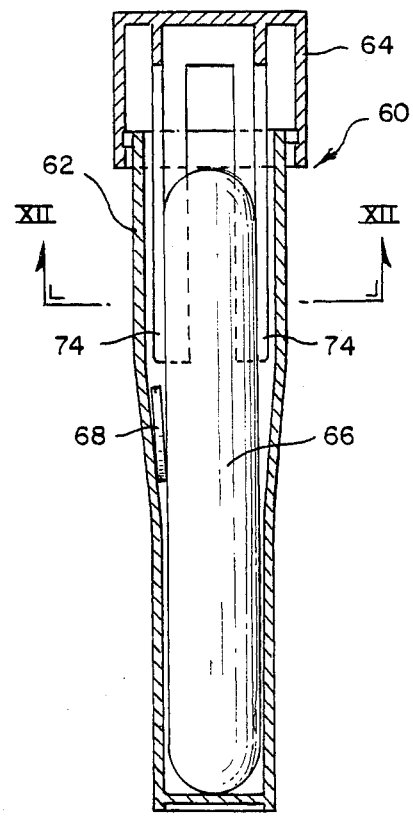
FIG. 11 is a sectional view of the biological indicator of FIG. 10.

The open ends are preferably in substantially abutting relationship to define seam 40 therebetween, but they need not touch. As shown in FIG. 2, inner tube 30 telescopes into the full depth of lower portion 24 and telescopes part way into upper portion 22. Inner tube 30 may, however, telescope only part way into lower portion 24 also. The outer surface of inner tube 30 is preferably smooth to permit an easy sliding contact between the exterior of inner tube 30 and the interior of the upper portion 22 of outer tube 20. There is a relatively close tolerance between the inner tube 30 and the upper and lower portions 22, 24 so that at least one, but, if desired, two tortuous paths may be defined which progress through the seam 40 between the interior of upper portion 22 and the exterior of inner tube 30 into housing 12 and/or through seam 40 between the interior of lower portion 24 and the exterior of inner tube 30 into housing 12. The tortuous paths impede the flow of sterilant into the interior of housing 12 to satisfy the AAMI recommendations and more closely simulate actual sterilization parameters. While two or more such tortuous paths are possible, at least one such tortuous path into housing 12 will suffice. For example, inner tube 30 may be sealed in any suitable manner to one of upper or lower portions 22, 24 to provide only one tortuous path through seam 40 to the interior of housing 12 so that unidirectional flow of sterilant into housing 12 is provided.

Upper portion 22 has a closed end 26. A hole 42 in end 26 is covered with an adhesive backed tab 44 which is impermeable to steam. Tab 44 permits the optional opening or closure of hole 42. Tab 44 seals hole 42 when test pack 10 is used to monitor steam sterilization cycles and is removed when test pack 10 is to be used to monitor ethylene oxide sterilization cycles. When in place, tab 44 seals hole 42 to prevent the entry of sterilant therethrough. The closed end 28 of lower portion 24 does not include a hole similar to that in end 26.

The outer surfaces of upper and lower portions 22, 24 may be lined with foil 34 or any other suitable means for making outer tube 20 nonabsorbent and impervious to sterilant penetration. Unless tab 44 is removed, entry of the sterilant is permitted only through seam 40 along the tortuous path or paths described above. In the preferred embodiment of test pack 10 a sterilant permeable layer 36, such as medical grade paper, preferably covers the entire outer tube 20 and, at least, seam 40. Sterilant permeates the layer 36 to enter the test pack 10 through seam 40. A chemical process indicator 38 and any desired labeling information may be printed on the layer 36. The chemical indicator 38 may be any suitable known indictor which will demonstrate whether the test pack 10 has been exposed to either steam or ethylene oxide sterilization conditions. Because different chemicals are required to indicate exposure to each type of sterilant, both chemicals are imprinted on the layer 36.

The interior surfaces 32 of tubes 20 and 30 are not lined or coated. The hydrophilic fiber board material is exposed to act as an absorbent for moisture present in both steam and ethylene oxide sterilization cycles, and as a heat sink to absorb the latent heat of the sterilant to slow the transfer of heat to the biological indicator 60. The fiber board is also absorbent to ethylene oxide.

Biological indicator 60 may be any suitable known biological indicator carrying microorganisms which are highly resistant to steam and ethylene oxide sterilization cycles. The preferred microorganisms are spores of Bacillus subtilis and spores of Bacillus stearothermophilus.

Biological indicator 60 includes an open ended ampule 62, a cap 64 adapted to enclose the open end of ampule 62 so that an annular space is defined between the interior surface of the cap 64 and the exterior surface of the ampule 62. A second tortuous path 70 is thus defined by the annular space into the interior of the ampule 62. A vial 66 of growth media, such as trypticase soy broth and a pH indicator dye, and a substrate 68 for the sterilization resistant microorganisms are enclosed in the ampule 62. Prongs 74 extend downwardly form cap 64 into ampule 62 to hold the vial 66 in place. Cap 64 has two positions. The first position permits the tortuous path 70 to remain open to admit the sterilant. The second position presses cap 64 downwardly to close the open end of ampule 62 and to press prongs 74 down over vial 66 to wedgedly engage vial 66 and thereby cause vial 66 to rupture. A preferred ampule is described in more detail in Dyke U.S. Pat. No. 4,304,869 which is hereby incorporated herein by reference. A second chemical process indicator may be imprinted on the outer surface of ampule 62 to indicate whether the ampule 62 has been exposed to either sterilant.

The means, such as carrier 50, for maintaining the position of biological indicator 60, is preferably made of plastic and includes a cut out section 52 into which biological indicator 60 is seated, cutaway portions 56 at each end and tips 54 adjacent to the cutaway portions 56. The tips 54 and cutaway portions 56 act as shock absorbers during shipping. Cutaway portions 56 also provide a convenient means for removing carrier 50 and biological indicator 60 from housing 12 at the conclusion of a sterilization cycle.

The fiber board material of housing 12 acts as a heat sink, a moisture and ethylene oxide absorbent and as an insulator to prevent the rapid warm up of the biological indicator. As indicated previously, the intent of test pack 10 is to provide a sterilant penetration, thermal and microbial challenge to both kinds of sterilization processes. The sterilization environment experienced by the most difficult to sterilize component of a chamber load must be simulated in the environment to which the spores on substrate 68 are exposed. The time required to kill the spores on substrate 68 should at least equal and preferably surpass the time required to kill microorganisms on the chamber load. Accordingly, means for slowing the rate at which the sterilant reaches the substrate 68 are provided by the tortuous paths, the heat sink, insulating and moisture absorbent properties of the fiber board, the ethylene oxide absorbent properties of the fiber board and the plastic carrier 50 and the heat sink properties of the cool liquid growth media in vial 66.

The design of test pack 10 of the present invention provides at least one tortuous path of sterilant flow toward the substrate 68. Steam, for example, enters through layer 36, seam 40, between inner tube 30 and the interior surface of upper portion 22 (and/or the interior surface of lower portion 24) into the interior of housing 12, then toward biological indicator 60 and the second tortuous path 70 defined by cap 64 and ampule 62 to substrate 68. Following removal of the tab 44, ethylene oxide enters through hole 42, and to a lesser extent through the path provided for the entry of steam. The ethylene oxide reaches the second tortuous path 70 and flows toward substrate 68.

The sterilant flow along the moisture absorbent surface of the tortuous path into housing 12 provided by test pack 10 of the present invention aids in sensitizing the device to the presence of noncondensable gases, such as air, into the sterilant. When, for example, steam comes in contact with the fiber board interior 32 along the tortuous path into housing 12, the latent heat from the steam is absorbed into the fiber board causing the steam to collapse. The condensate is then absorbed into the fiber board, leaving any air mixed with the steam remaining. The collapse of the steam draws in more steam which forces the air, if any, into housing 12. The air, if present, will enter ampule 60 to simulate the steam/air mix present in the sterilizer.

Test packs were prepared for steam and ethylene oxide sterilization cycles according to the AAMI recommendations for such test packs. Two biological indicators 60 and two spore strips enclosed in a glassine envelope were placed in each AAMI type test pack. Test packs 10 of the present invention and the appropriate AAMI type test packs were exposed, side by side, to steam and ethylene oxide sterilization cycles at varying times to develop a resistance profile for each test pack. All test results are expressed as percent positive units/no. of units exposed for each exposure time and sterilization cycle type.

Figure 13:
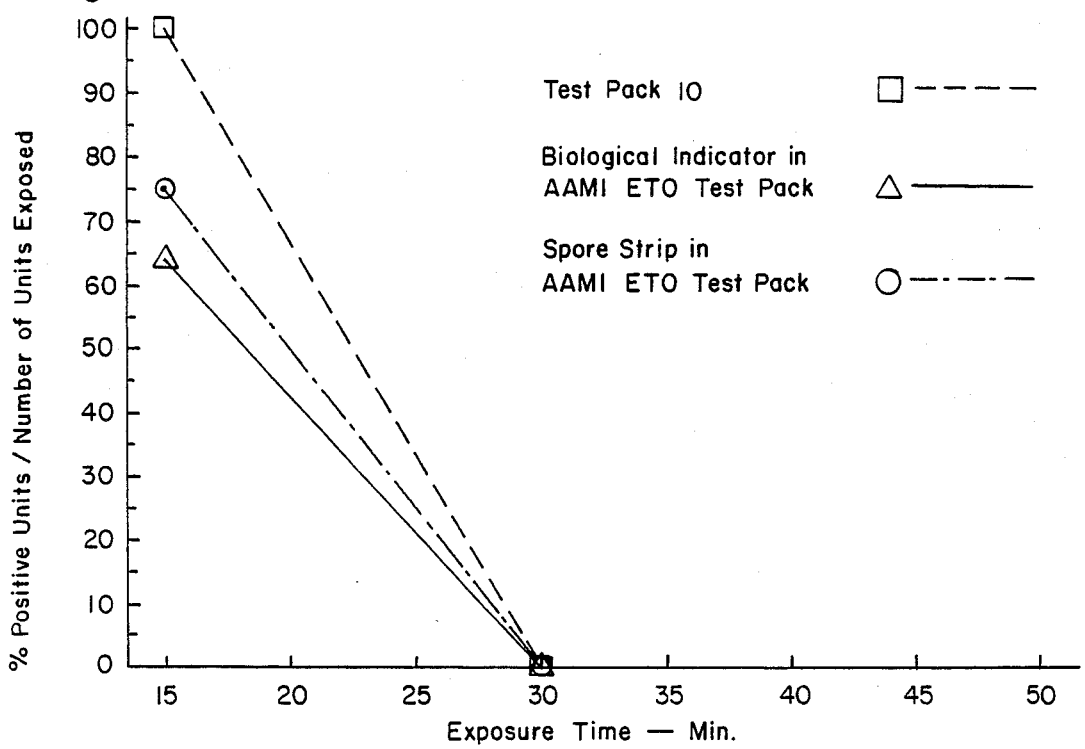
FIGS. 13 and 14 are graphs illustrating the results of comparative tests of the test packs of the present invention and AAMI recommended test packs in ethylene oxide sterilizers.

In a first series of tests, 120 test packs 10 per exposure were tested with AAMI packs in a 20×20×38 ethylene oxide sterilizer at 130° F., 60% relative humidity and 600 mg ethylene oxide per liter ±10%. The results are illustrated in FIG. 13, and in Table I below.

TABLE I

| Exposure Time (min) | Test Pack 10 (%) | AAMI Test Packs | |
|---|---|---|---|
| | | Bio Indicator 60 (%) | Spore Strip (%) |
| 15 | 100 | 64 | 75 |
| 30 | 0 | 0 | 0 |
| 40 | 0 | 0 | 0 |
| 50 | 0 | 0 | 0 |

Figure 14:
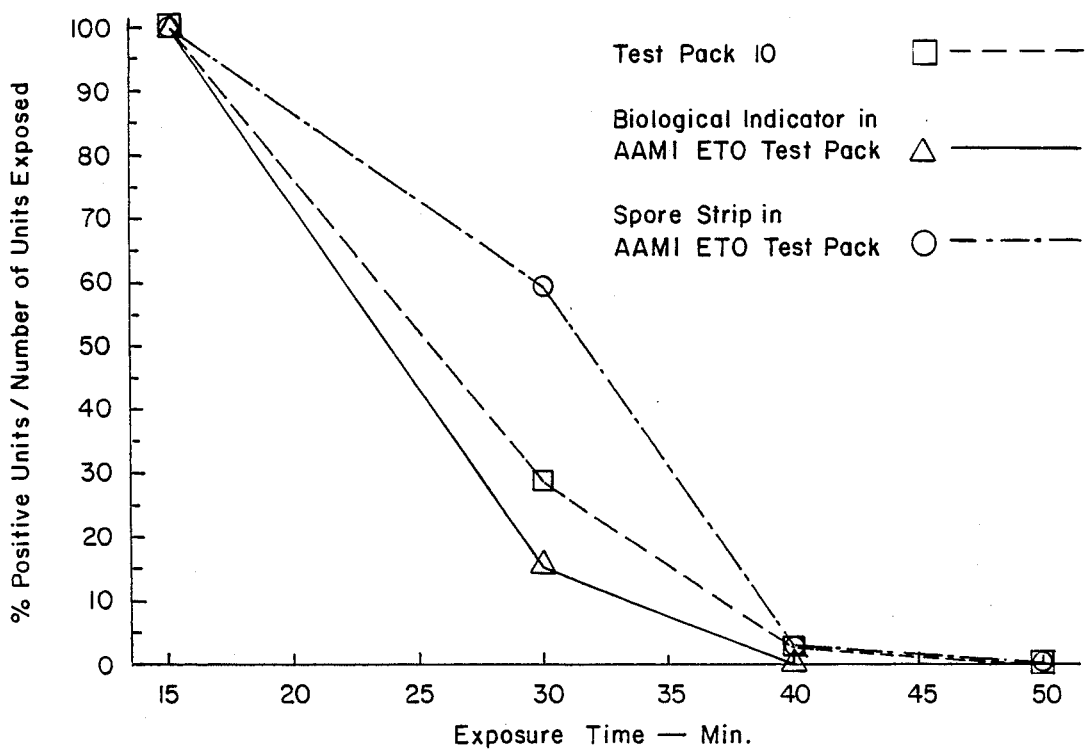

In a second series of tests, 70 test packs 10 per exposure were exposed to ethylene oxide sterilization cycles side by side with AAMI test packs in a Biological Indicator Evaluation Resistometer at 130° F., 60% relative humidity and 600 mg ethylene oxide per liter ±10%. The results are shown in FIG. 14 and in Table II below.

TABLE II

| Exposure Time (min) | Test Pack 10 (%) | AAMI Test Packs | |
|---|---|---|---|
| | | Bio Indicator 60 (%) | Spore Strip (%) |
| 15 | 100 | 100 | 100 |
| 30 | 28.6 | 15.6 | 59.4 |
| 40 | 2.8 | 0 | 3.0 |
| 50 | 0 | 0 | 0 |

Figure 15:
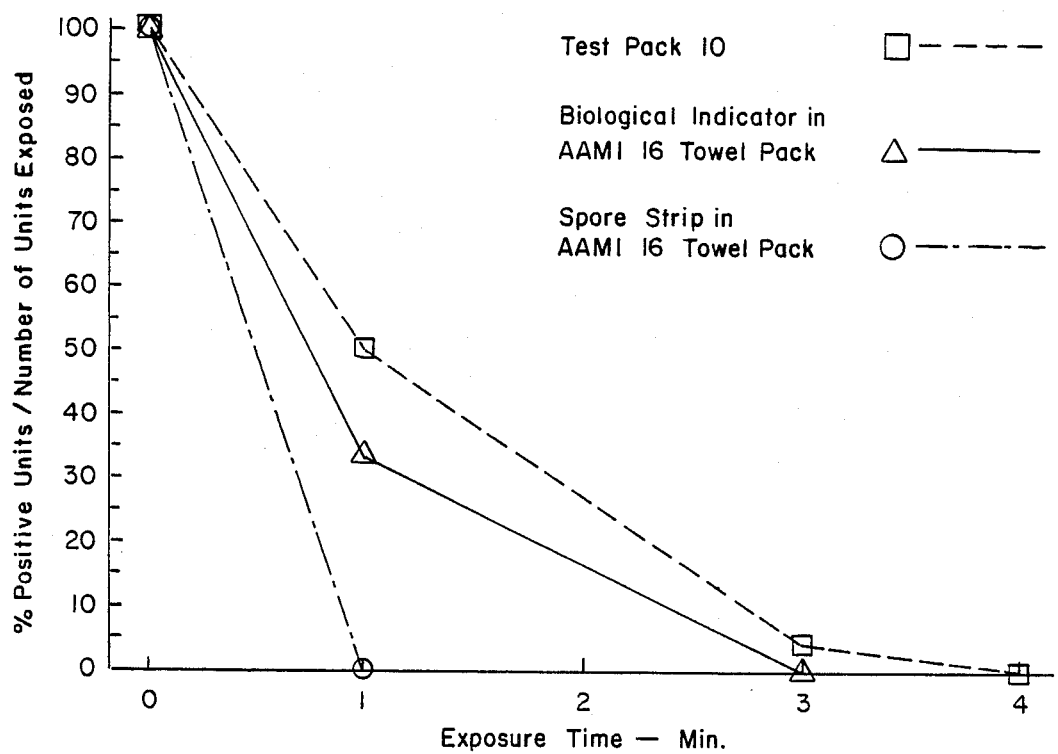
FIGS. 15 and 16 are graphs illustrating the results of comparative tests of the test packs of the present invention and AAMI recommended test packs in steam sterilizers.

In a third series of tests, 140 test packs 10 per exposure were tested with AAMI 16 towel test packs in a 270° F. prevacuum steam sterilizer. The results are shown in FIG. 15 and in Table III below.

TABLE III

| Exposure Time (min) | Test Pack 10 (%) | AAMI Test Packs | |
|---|---|---|---|
| | | Bio Indicator 60 (%) | Spore Strip (%) |
| 0 | 100 | 100 | 100 |
| 1 | 50 | 33 | 0 |
| 3 | 4.3 | 0 | 0 |
| 4 | 0 | 0 | 0 |

Figure 16:
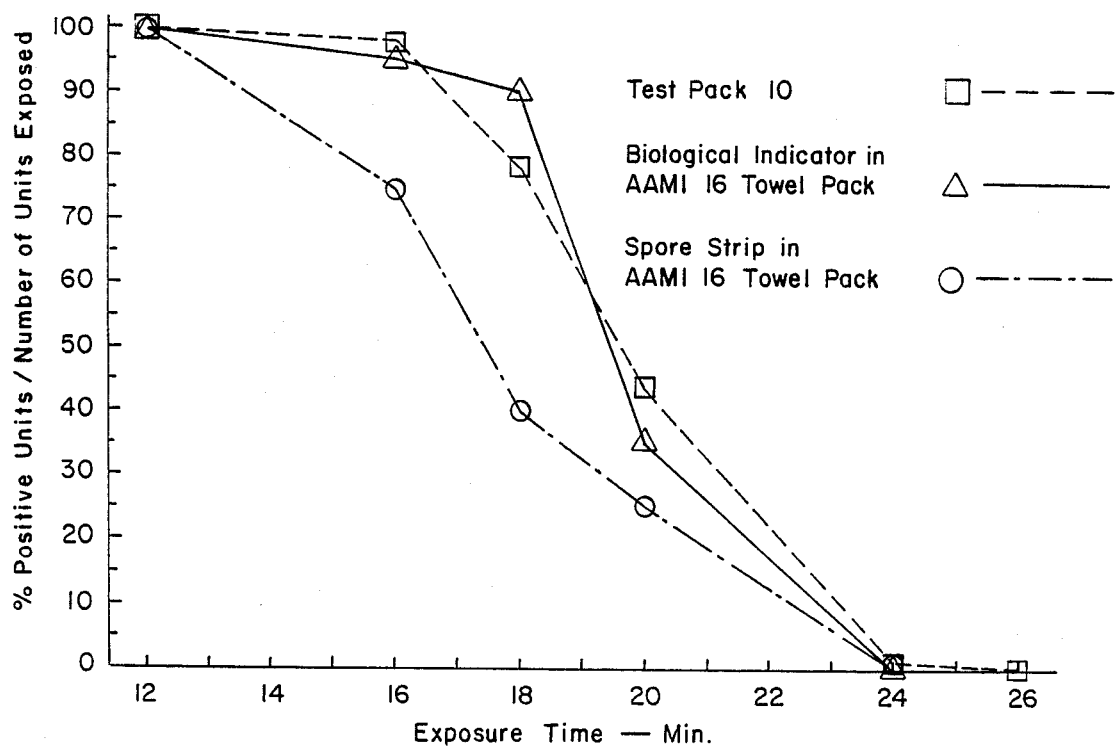

In a fourth series of tests 170 test packs 10 per exposure were tested with AAMI 16 towel test packs in a 250° F. gravity displacement steam sterilizer. The results are shown in FIG. 16 and in Table IV below.

TABLE IV

| Exposure Time (min) | Test Pack 10 (%) | AAMI Test Packs | |
|---|---|---|---|
| | | Bio Indicator 60 (%) | Spore Strip (%) |
| 12 | 100 | 100 | 100 |
| 16 | 97.0 | 95.0 | 75.0 |
| 18 | 78.2 | 90.0 | 40.0 |
| 20 | 43.5 | 35.0 | 25.0 |
| 24 | 1.0 | 0 | 0 |
| 26 | 0 | 0 | 0 |

A comparison of test pack 10 of the present invention to test packs recommended by AAMI for steam and ethylene oxide sterilization monitoring in a few different types of sterilizers demonstrates that test pack 10 functions in accordance with the AAMI recommendations for both steam and ethylene oxide sterilization cycles.

The test pack 10 provides an economical, disposable device which can be used to monitor the efficacy of either steam or ethylene oxide sterilization cycles. Hospitals and other health care facilities can thus simplify their inventories of test packs because only one device need be ordered for both types of sterilization monitoring. Although test pack 10 has been described in terms of a tubular shape, those skilled in the art will recognize that any shape which permits the flow of sterilant through a tortuous path dimensioned to promote intimate contact between the sterilant and the moisture absorbent surface of the tortuous path comes within the scope of the instant invention.

What is claimed is:

1. A device for monitoring the efficacy of steam and ethylene oxide sterilization cycles comprising:
    a housing having an interior made of a material having heat sink, insulating and moisture absorbent properties, said housing being configured to define at least one tortuous path for entry of sterilant into said housing, said tortuous path having a moisture absorbent surface and being dimensioned to promote intimate contact between said sterilant and said surface as said sterilant moves along said tortuous path;
    means for optionally providing an alternate path of entry of sterilant into said housing; and
    a biological indicator within said housing which includes a calibration of microbes which are resistant to sterilization by steam and ethylene oxide.

2. The device recited in claim 1 wherein said housing has an inner member and an outer member, said outer member having an upper portion and a lower portion, each said upper and lower portion having one open end in a substantially abutting relationship with said open end of said other portion to define a seam therebetween; and said inner member telescoping into said upper portion and into said lower portion past said seam to define at least one said tortuous path progressing through said seam, between the outer surface of said inner member and the inner surfaces of at least one of said upper and lower portions and into said housing.

3. The device recited in claim 1 wherein said means for optionally providing an alternate path of entry of sterilant is a hole in said housing and an optionally removable closure for sealing said hole until said closure is removed.

4. The device recited in claim 1 wherein said biological indicator comprises:

an ampule having one open end;

a cap for covering said open end of said ampule, said cap dimensioned to define an annular space between the interior of said cap and the exterior of said ampule to provide a second tortuous path for entry of sterilant into said ampule, said cap having two positions, one said position permitting entry of sterilant through said second tortuous path and the other said position closing said ampule;

a substrate inoculated with a calibration of bacterial spores resistant to sterilization by steam and ethylene oxide; and an enclosed frangible vial of growth media for said spores.

5. The device recited in claim 1 further comprising a means for positioning said biological indicator within said housing.

6. The device recited in claim 5 wherein said positioning means is a carrier having a cutout section for holding said biological indicator.

7. The device recited in claim 6 wherein said carrier further comprises shock absorbing means at the ends of said carrier.

8. A device for monitoring the efficacy of steam and ethylene oxide sterilization cycles comprising:

a housing having an inner member and an outer member, said outer member having a first entryway therethrough to at least one tortuous path defined between said inner and outer members, said tortuous path having a moisture absorbent surface and being dimensioned to promote intimate contact between said sterilant and said surface as said sterilant moves along said tortuous path;

said housing having an alternate entryway therethrough;

means removably sealing said alternate entryway for optionally providing a second path of entry of sterilant into said housing; and a biological indicator within said housing which includes a calibration of microbes which are resistant to sterilization by steam and ethylene oxide.

9. The device recited in claim 8 wherein said housing is made from a cellulosic material having heat sink, insulating and moisture and ethylene oxide absorbent properties.

10. The device recited in claim 8 wherein the exterior of said housing, excluding said first entryway, is covered with a moisture repelling material which is impermeable to steam and ethylene oxide sterilants.

11. The device recited in claim 8 wherein at least said first entryway is covered with a layer of material which is permeable to steam and ethylene oxide sterilants.

12. The device recited in claim 8 further comprising means for positioning said biological indicator.

13. The device recited in claim 12 wherein said positioning means is a carrier made of an ethylene oxide absorbent material.

* * * * *

UNITED STATES PATENT AND TRADEMARK OFFICE
CERTIFICATE OF CORRECTION

PATENT NO. : 4,839,291

DATED : June 13, 1989

INVENTOR(S) : Jon D. Welsh and Denis G. Dyke

It is certified that error appears in the above-identified patent and that said Letters Patent is hereby corrected as shown below:

Col. 3, line 34, delete "commenced" and substitute therefor --commended--.

Col. 6, line 13, delete "form" and substitute therefor --from--.

Signed and Sealed this

Sixth Day of March, 1990

*Attest:*

JEFFREY M. SAMUELS

*Attesting Officer*   *Acting Commissioner of Patents and Trademarks*